US008785683B2

(12) United States Patent
Boussie et al.

(10) Patent No.: US 8,785,683 B2
(45) Date of Patent: Jul. 22, 2014

(54) PRODUCTION OF GLUTARIC ACID AND DERIVATIVES FROM CARBOHYDRATE-CONTAINING MATERIALS

(75) Inventors: Thomas R. Boussie, Menlo Park, CA (US); Eric L. Dias, Belmont, CA (US); Zachary M. Fresco, Redwood City, CA (US); Vincent J. Murphy, San Jose, CA (US)

(73) Assignee: Rennovia, Inc., Menlo Park, CA (US)

( * ) Notice: Subject to any disclaimer, the term of this patent is extended or adjusted under 35 U.S.C. 154(b) by 379 days.

(21) Appl. No.: 12/814,216

(22) Filed: Jun. 11, 2010

(65) Prior Publication Data

US 2010/0317825 A1    Dec. 16, 2010

Related U.S. Application Data

(60) Provisional application No. 61/268,414, filed on Jun. 13, 2009.

(51) Int. Cl.
*C07C 51/377* (2006.01)

(52) U.S. Cl.
USPC .......................................................... 562/515

(58) Field of Classification Search
CPC ........ C07C 55/12; C07C 69/42; C07C 51/377
See application file for complete search history.

(56) References Cited

U.S. PATENT DOCUMENTS

| | | | |
|---|---|---|---|
| 2,472,168 A | 6/1949 | Mehltretter et al. |
| 2,750,394 A | 6/1956 | Peniston |
| 2,851,468 A | 9/1958 | Snyder |
| 2,917,520 A | 12/1959 | Cope |
| 2,929,823 A | 3/1960 | Garber et al. |
| 3,070,633 A | 12/1962 | Utne et al. |
| 3,083,236 A | 3/1963 | Utne et al. |
| 3,118,912 A | 1/1964 | Smith |
| 3,189,651 A | 6/1965 | Garber et al. |
| 3,225,066 A | 12/1965 | Baak |
| 3,326,944 A | 6/1967 | Baak |
| 3,483,228 A | 12/1969 | Garber et al. |
| 3,607,922 A | 9/1971 | Acres et al. |
| 3,671,566 A | 6/1972 | Decker et al. |
| 3,761,579 A | 9/1973 | Curtis, Jr. et al. |
| 3,860,626 A | 1/1975 | Putnin et al. |
| 3,873,614 A | 3/1975 | Lamberti et al. |
| 3,896,056 A | 7/1975 | Benjamin et al. |
| 3,917,707 A | 11/1975 | Williams et al. |
| 4,067,900 A | 1/1978 | Intille |
| 4,078,139 A | 3/1978 | Barton et al. |
| 4,302,432 A | 11/1981 | Polichnowski |
| 4,337,202 A | 6/1982 | Hearon et al. |
| 4,339,387 A | 7/1982 | Fleche et al. |
| 4,363,815 A | 12/1982 | Yu et al. |
| 4,400,468 A | 8/1983 | Faber |
| 4,401,823 A | 8/1983 | Arena |
| 4,439,551 A | 3/1984 | Yeakey et al. |
| 4,533,743 A | 8/1985 | Medeiros et al. |
| 4,590,283 A | 5/1986 | Gaset et al. |
| 4,605,790 A | 8/1986 | Wojtkowski |
| 4,722,997 A | 2/1988 | Roerdink et al. |
| 4,740,605 A | 4/1988 | Rapp |
| 4,767,856 A | 8/1988 | Dockner et al. |
| 4,820,880 A | 4/1989 | Urbas |
| 4,833,230 A | 5/1989 | Kiely et al. |
| 4,843,173 A | 6/1989 | Saito et al. |
| 4,845,208 A | 7/1989 | Fuertes et al. |
| 4,900,407 A | 2/1990 | Saito et al. |
| 4,912,237 A | 3/1990 | Zeitsch |
| 4,971,657 A | 11/1990 | Avignon et al. |
| 4,977,283 A | 12/1990 | Leupold et al. |
| 5,071,754 A | 12/1991 | Walkup et al. |
| 5,132,452 A | 7/1992 | Deller et al. |
| 5,132,456 A | 7/1992 | King et al. |
| 5,149,680 A | 9/1992 | Kitson et al. |
| 5,196,617 A | 3/1993 | Kovenklioglu et al. |
| 5,247,012 A | 9/1993 | Vyvoda |
| 5,252,473 A | 10/1993 | Walkup et al. |
| 5,264,624 A | 11/1993 | Vogtel et al. |
| 5,276,240 A | 1/1994 | Timmons et al. |
| 5,281,647 A | 1/1994 | Eapen |
| 5,290,852 A | 3/1994 | Vyvoda |
| 5,359,137 A | 10/1994 | Burke |

(Continued)

FOREIGN PATENT DOCUMENTS

| | | |
|---|---|---|
| CA | 2097812 A1 | 6/1992 |
| CN | 101486639 | 7/2009 |

(Continued)

OTHER PUBLICATIONS

White et al, Basic Energy Sciences Advisory Committee Subpanel Workshop Report, Opportunities for Catalysis in the 21st Century, 2002, pp. 1-47.*
Casanova, O., et al., "Biomass into Chemicals: Aerobic Oxidation of 5-Hydroxymethyl-2-Furfural into 2,5-Furandicarboxylic Acid with Gold Nanoparticle Catalysts," 2009, ChemSusChem, 2:1138-1144.
Clarke, J.K.A., et al., "Preparation of Supported Platinum-Gold Catalysts and Alkane Reactions on Selected Platinum and Platinum-Gold Supported Clusters," 1984, App Catalysis, 9:85-108.
Dimitratos, N., et al., "Synergetic Effect of Platinum or Palladium on Gold Catalyst in the Selective Oxidation of D-Sorbitol," 2005, Catalysis Letters, 99:3-4:181-185.
Dirkx, J., et al., "The Preparation of D-Glucaric Acid by the Oxidation of D-Gluconic Acid Catalysed by Platinum on Carbon," 1977, Carbohydrate Research, 59:63-72.

(Continued)

*Primary Examiner* — Paul A Zucker
(74) *Attorney, Agent, or Firm* — Senniger Powers LLP

(57) ABSTRACT

The present invention generally relates to processes for the chemocatalytic conversion of a pentose source to a glutaric acid product. The present invention includes processes for the conversion of pentose to a glutaric acid product via pentaric acid or derivatives thereof. The present invention also includes processes comprising the catalytic oxidation of pentose to pentaric acid and catalytic hydrodeoxygenation of pentaric acid or derivatives thereof to a glutaric acid product.

36 Claims, No Drawings

(56) References Cited

U.S. PATENT DOCUMENTS

| | | |
|---|---|---|
| 5,426,219 A | 6/1995 | Lehnhardt et al. |
| 5,426,252 A | 6/1995 | Sherif |
| 5,430,214 A | 7/1995 | Smith et al. |
| 5,434,233 A | 7/1995 | Kiely et al. |
| 5,484,914 A | 1/1996 | Skibida et al. |
| 5,487,987 A | 1/1996 | Frost et al. |
| 5,516,960 A | 5/1996 | Robinson |
| 5,562,777 A | 10/1996 | Farone et al. |
| 5,599,977 A | 2/1997 | Kiely et al. |
| 5,616,496 A | 4/1997 | Frost et al. |
| 5,625,110 A | 4/1997 | Schoedel et al. |
| 5,683,952 A | 11/1997 | Onozawa et al. |
| 5,721,189 A | 2/1998 | Zhang |
| 5,726,046 A | 3/1998 | Farone et al. |
| 5,731,467 A | 3/1998 | Fleche |
| 5,766,439 A | 6/1998 | Eyal et al. |
| 5,772,013 A | 6/1998 | Kunz et al. |
| 5,773,677 A | 6/1998 | Lansink-Rotgerink et al. |
| 5,789,333 A | 8/1998 | Angelici et al. |
| 5,811,628 A | 9/1998 | Weber et al. |
| 5,820,687 A | 10/1998 | Farone et al. |
| 5,900,511 A | 5/1999 | Sengupta et al. |
| 5,919,994 A | 7/1999 | Rao |
| 5,922,635 A | 7/1999 | Olah et al. |
| 5,981,420 A | 11/1999 | Nakano et al. |
| 5,986,127 A | 11/1999 | Ionkin et al. |
| 5,998,657 A | 12/1999 | Gogate et al. |
| 6,008,418 A | 12/1999 | Baur et al. |
| 6,028,025 A | 2/2000 | Ying et al. |
| 6,049,004 A | 4/2000 | Kiely et al. |
| 6,087,296 A | 7/2000 | Harper |
| 6,127,585 A | 10/2000 | Duzick et al. |
| 6,147,208 A | 11/2000 | Achhammer et al. |
| 6,180,830 B1 | 1/2001 | Jacquot |
| 6,228,800 B1 | 5/2001 | Yamaguchi et al. |
| 6,232,264 B1 | 5/2001 | Lukehart et al. |
| 6,391,821 B1 | 5/2002 | Satoh et al. |
| 6,403,521 B1 | 6/2002 | Ishii et al. |
| 6,436,866 B1 | 8/2002 | Nishikido et al. |
| 6,441,202 B1 | 8/2002 | Lightner |
| 6,444,608 B1 | 9/2002 | Oki et al. |
| 6,462,220 B1 | 10/2002 | Luyken et al. |
| 6,476,260 B1 | 11/2002 | Herrmann et al. |
| 6,495,730 B1 | 12/2002 | Konishi et al. |
| 6,498,269 B1 | 12/2002 | Merbouh et al. |
| 6,500,649 B2 | 12/2002 | Fouache et al. |
| 6,518,440 B2 | 2/2003 | Lightner |
| 6,521,779 B1 | 2/2003 | Boschat et al. |
| 6,559,275 B2 | 5/2003 | Minami et al. |
| 6,569,670 B2 | 5/2003 | Anderson et al. |
| 6,569,802 B1 | 5/2003 | Ionkin |
| 6,692,578 B2 | 2/2004 | Schmidt et al. |
| 6,716,339 B2 | 4/2004 | Liu et al. |
| 6,743,928 B1 | 6/2004 | Zeitsch |
| 6,773,512 B2 | 8/2004 | Ennelin et al. |
| 6,894,135 B2 | 5/2005 | Kiely et al. |
| 6,894,160 B2 | 5/2005 | Capan et al. |
| 6,897,338 B2 | 5/2005 | Zhong et al. |
| 6,953,873 B2 | 10/2005 | Cortright et al. |
| 6,958,405 B2 | 10/2005 | Le-Khac et al. |
| 7,084,090 B2 | 8/2006 | Ishii et al. |
| 7,115,541 B2 | 10/2006 | Ishii et al. |
| 7,138,035 B2 | 11/2006 | Cui et al. |
| 7,161,005 B2 | 1/2007 | Schlingloff et al. |
| 7,166,743 B2 | 1/2007 | Zhong et al. |
| 7,179,366 B2 | 2/2007 | Harle et al. |
| 7,317,116 B2 | 1/2008 | Sanborn |
| 7,344,696 B2 | 3/2008 | Canos et al. |
| 7,354,743 B2 | 4/2008 | Vlasenko et al. |
| 7,364,880 B2 | 4/2008 | Ray et al. |
| 7,371,894 B2 | 5/2008 | Wonders et al. |
| 7,385,081 B1 | 6/2008 | Gong |
| 7,393,676 B2 | 7/2008 | Gokarn et al. |
| 7,399,855 B2 | 7/2008 | Frost |
| 7,411,078 B2 | 8/2008 | Miura et al. |
| 7,413,882 B2 | 8/2008 | Berka et al. |
| 7,432,382 B2 | 10/2008 | Sanborn et al. |
| 7,459,597 B2 | 12/2008 | Koivusalmi et al. |
| 7,517,675 B2 | 4/2009 | Vercauteren et al. |
| 7,572,925 B2 | 8/2009 | Dumesic et al. |
| 7,579,489 B2 | 8/2009 | Sanborn |
| 7,579,490 B2 | 8/2009 | Sanborn et al. |
| 7,582,444 B2 | 9/2009 | Hughes |
| 7,608,689 B2 | 10/2009 | Harris et al. |
| 2002/0111458 A1 | 8/2002 | Minami et al. |
| 2003/0015457 A1 | 1/2003 | Liu et al. |
| 2005/0009694 A1 | 1/2005 | Watts et al. |
| 2005/0233423 A1 | 10/2005 | Berka et al. |
| 2005/0272134 A1 | 12/2005 | Hughes |
| 2006/0084800 A1 | 4/2006 | Chenault |
| 2006/0084817 A1 | 4/2006 | Chenault |
| 2007/0027341 A1 | 2/2007 | Rossi et al. |
| 2007/0031918 A1 | 2/2007 | Dunson, Jr. et al. |
| 2007/0031919 A1 | 2/2007 | Dunson, Jr. et al. |
| 2007/0111294 A1 | 5/2007 | Burgard et al. |
| 2007/0166220 A1 | 7/2007 | Ceyer et al. |
| 2007/0193960 A1 | 8/2007 | Frank et al. |
| 2007/0215484 A1 | 9/2007 | Peterson et al. |
| 2007/0219397 A1 | 9/2007 | Holladay et al. |
| 2007/0287845 A1 | 12/2007 | Lilga et al. |
| 2008/0033187 A1 | 2/2008 | Zhao et al. |
| 2008/0033188 A1 | 2/2008 | Dumesic et al. |
| 2008/0033205 A1 | 2/2008 | Kiely et al. |
| 2008/0041366 A1 | 2/2008 | Wahnon |
| 2008/0096242 A1 | 4/2008 | Sanders et al. |
| 2008/0103232 A1 | 5/2008 | Lake et al. |
| 2008/0103318 A1 | 5/2008 | Lilga et al. |
| 2008/0103340 A1 | 5/2008 | Binder et al. |
| 2008/0206562 A1 | 8/2008 | Stucky et al. |
| 2008/0216391 A1 | 9/2008 | Cortright et al. |
| 2008/0293109 A1 | 11/2008 | Berka et al. |
| 2008/0300434 A1 | 12/2008 | Cortright et al. |
| 2008/0300435 A1 | 12/2008 | Cortright et al. |
| 2009/0018300 A1 | 1/2009 | Bloom et al. |
| 2009/0047719 A1 | 2/2009 | Burgard et al. |
| 2009/0131259 A1 | 5/2009 | Kiely et al. |
| 2009/0171037 A1 | 7/2009 | Aoshima et al. |
| 2009/0211942 A1 | 8/2009 | Cortright et al. |
| 2009/0215128 A1 | 8/2009 | Vlasenko et al. |
| 2009/0250653 A1 | 10/2009 | Kiely et al. |
| 2009/0255171 A1 | 10/2009 | Dumesic et al. |
| 2009/0270245 A1 | 10/2009 | Kumar et al. |
| 2009/0305364 A1 | 12/2009 | Burgard et al. |
| 2010/0113263 A1 | 5/2010 | Lee et al. |

FOREIGN PATENT DOCUMENTS

| | | |
|---|---|---|
| DE | 19609069 A1 | 9/1997 |
| EP | 0096913 A1 | 12/1983 |
| EP | 0151498 A2 | 8/1986 |
| EP | 1728844 A1 | 12/2006 |
| EP | 2033958 A1 | 3/2009 |
| FR | 2556344 A1 | 6/1985 |
| FR | 2663933 A1 | 1/1992 |
| FR | 2664273 A1 | 1/1992 |
| FR | 2669635 A1 | 5/1992 |
| GB | 591858 | 9/1947 |
| GB | 600871 | 4/1948 |
| GB | 876463 | 9/1961 |
| GB | 1044883 | 10/1966 |
| JP | 33-7620 | 8/1958 |
| JP | 53-144506 | 12/1978 |
| JP | 55-013243 | 1/1980 |
| JP | 59-190984 | 10/1984 |
| JP | 2-088569 A | 3/1990 |
| JP | 2001-316311 A | 11/2001 |
| JP | 2002-308819 A | 10/2002 |
| JP | 2005-060447 A | 3/2005 |
| JP | 2005-200321 A | 7/2005 |
| JP | 2005-232116 A | 9/2005 |
| JP | 2007-145736 A | 6/2007 |
| LV | 10857 B | 8/1996 |
| WO | 8201701 A1 | 5/1982 |
| WO | 9421690 A2 | 9/1994 |

(56) References Cited

FOREIGN PATENT DOCUMENTS

| WO | 9507996 A1 | 3/1995 |
|---|---|---|
| WO | 9604224 A1 | 2/1996 |
| WO | 9638402 A1 | 12/1996 |
| WO | 2005003072 A1 | 1/2005 |
| WO | 2006005070 A1 | 1/2006 |
| WO | 2006100584 A2 | 9/2006 |
| WO | 2006119357 A2 | 11/2006 |
| WO | 2007075370 A2 | 7/2007 |
| WO | 2007075476 A2 | 7/2007 |
| WO | 2007089677 A2 | 8/2007 |
| WO | 2007141293 A1 | 12/2007 |
| WO | 2008021054 A2 | 2/2008 |
| WO | 2008070762 A1 | 6/2008 |
| WO | 2008109877 A1 | 9/2008 |
| WO | 2008144514 A2 | 11/2008 |

OTHER PUBLICATIONS

Ibert, M., et al., "Determination of the Side-Products Formed During the Nitroxide-Mediated Bleach Oxidation of Glucose to Glucaric Acid," 2002, Carbohydrate Res, 337:1059-1063.

Lewkowski, J., "Synthesis, Chemistry and Applications of 5-Hydroxymethylfurfural and its Derivatives," 2001, Arkivoc (i):17-54.

Mallat, T., et al., "Oxidation of Alcohols with Molecular Oxygen on Solid Catalysts," 2004, Chem Rev, 104:3037-3058.

Mamman, A.S., et al. "Furfural: Hemicellulose/xylose-Derived Biochemical," 2008, Biofuels, Bioprod. Bioref., 2:438-454.

Mehltretter, C.L., et al., "Sugar Oxidation, Saccharic and Oxalic Acids by the Nitric Acid Oxidation of Dextrose," 1953, Ag and Food Chem, 1/12:779-783.

Merbouh, N., et al., "Facile Nitroxide-mediated Oxidations of D-Glucose to D-Glucaric Acid," 2001, Carbohydrate Res, 336:75-78.

Moore, J.A., et al., "An Improved Hydrogenation for the Preparation of Tetrahydrofuran cis-2,5-Dicarboxylic Acid," 1972, Organic Preparations and Procedures Int., 4/6:289-292.

Moreau, C., et al., "Recent Catalytic Advances in the Chemistry of Substituted Furans from Carbohydrates and in the Ensuing Polymers," 2004, Topics in Catalysis, 27/1-4:11-30.

Niu, W., et al., "Benzene-Free Synthesis of Adipic Acid," 2002, Biotechnol Prog, 18:201-211.

Ortiz-Soto, L.B., et al., "Structure-Sensitivity of Propylene Hydrogenation Over Cluster-Derived Bimetallic Pt-Au Catalysts," 2006, Catalysis Letters, 107/1-2:13-17.

Pamuk, V., et al., "The Preparation of D-Glucaric Acid by Oxidation of Molasses in Packed Beds," 2001, J Chem Technol Biotechnol, 76:186-190.

Prati, L., et al., "Effect of Gold Addition on Pt and Pd Catalysts in Liquid Phase Oxidations," 2007, Topics in Catalysis, 44/1-2:319-324.

Röper, H., "Selective Oxidation of D-Glucose: Chiral Intermediates for Industrial Utilization," 1991, Carbohydrates as Organic Raw Materials, F.W. Lichtenhaler (Ed), Verlag Chemie, Weinheim, Germany, pp. 267-288.

Shen, Y., et al., "Efficient Synthesis of Lactic Acid by Aerobic Oxidation of Glycerol on Au-Pt/TiO2 Catalysts," 2010, Chem Eur J, 16:7368-7371.

Smits, P.C.C., et al., "The Selective Oxidation of Aldoses and Aldonic Acids to 2-Ketoaldonic Acids with Lead-Modified Platinum-on-Carbon Catalysts," 1986, Carbohydrate Res, 153:227-235.

Smits, P.C.C., et al., "Lead Modified Platinum on Carbon Caralysts for the Selective Oxidation of (2-) Hydroxycarbonic Acids, and Especially Polyhydroxycarbonic Acids to Their 2-Keto Derivatives," 1987, App Catalysis, 33:83-96.

Thaburet, J-F., et al., "TEMPO-mediated Oxidation of Maltodextrins and D-Glucose: Effect of pH on the Selectivity and Sequestering Ability of the Resulting Polycarboxylates," 2001, Carbohydrate Res, 330:21-29.

Wenkin, M., et al., "Influence of Metallic Precursors on the Properties of Carbon-Supported Bismuth-Promoted Palladium Catalysts for the Selective Oxidation of Glucose to Gluconic Acid," 1996, App Catalysis A: General, 148:181-199.

Yong, G., et al., "Efficient Catalytic System for the Selective Production of 5-Hydroxymethylfurfural from Glucose and Fructose," 2008, Angew Chem Int Ed, 47:9345-9348.

Dijkgraaf, P.J.M., "Oxidation of Glucose to Glucaric Acid by Pt/C Catalysts," 1989, 105 pages, Thesis, Technische Universiteit Eindhoven.

Lichtenthaler, F.W., et al., "Carbohydrates as Green Raw Materials for the Chemical Industry," 2004 C.R. Chimie 7:65-90.

Merbouh, N., et al., "4-AcNH-TEMPO-Catalyzed Oxidation of Aldoses to Aldaric Acids Using Chlorine or Bromine as Terminal Oxidants," 2002, J Carbohydrate Chem, 21/1&2: 65-77.

International Search Report issued in PCT/US2010/060143 dated Apr. 5, 2011, 6 pages.

Written Opinion issued in PCT/US2010/060143 dated Apr. 5, 2011, 9 pages.

Scifinder Search Results on "Xylaric Acid" —search conducted on Mar. 15, 2010, 11 Pages.

Habrioux, A., et al., "Activity of Platinum-Gold Alloys for Glucose Electrooxidation in Biofuel Cells," 2007, J Phys Chem B, 111:10329-10333.

Kerzenmacher, S., et al., "Energy Harvesting by Implantable Abiotically Catalyzed Glucose Fuel Cells," 2008, J Power Sources, 182:1-17.

Second Written Opinion issued in PCT/US2010/060143 dated May 30, 2012, 6 pages.

Abbadi, A., et al., "Effect of pH in the Pt-Catalyzed Oxidation of D-Glucose to D-Gluconic Acid," 1995, J. Mol. Catal. A: Chem., 97:111-118.

Abbadi, A., et al., "Highly Selective Oxidation of Aldonic Acids to 2-Keto-Aldonic Acids Over Pt-Bi and Pt-Pb Catalysts," 1995, App. Catal. A: General, 124:409-417.

Blanc, B., et al., "Starch-Derived Polyols for Polymer Technologies: Preparation by Hydrogenolysis on Metal Catalysts," Apr. 2000, Green Chemistry, pp. 89-91.

Brown, J.M., Equilibration of D-Glucaric Acid in Aqueous Solution, 2007, Thesis, University of Waikato, 191 pages.

Dirkx, J., et al., "The Oxidation of Glucose with Platinum on Carbon as Catalyst," 1981, J. Catal., 67:1-13.

Dirkx, J., et al., "The Oxidation of Gluconic Acid with Platinum on Carbon as Catalyst," 1981, J. Catal., 67:14-20.

Gehret, T. et al., "Convenient Large-Scale Synthesis of D-Glucaro-1,4:6,3-dilactone," 2009, J. Org. Chem., 74 (21), pp. 8373-8376.

Koso, S., et al., "Chemoselective Hydrogenolysis of Tetrahydrofurfuryl Alcohol to 1,5-Pentanediol," 2009, Chem. Commun., 2035-2037.

Koso, S., et al., "Promoting Effect of Mo on the Hydrogenolysis of Tetrahydrofurfuryl Alcohol to 1,5-pentanediol Over Rh/SiO2," 2009, J. Catal., 267:89-92.

Abstract of BG 100407, EPISUCRES SA, 1997, 1 page.

Saha, B.C., "Hemicellulose Bioconversion," J. Ind. Microbiol. Biotechnol., 2003, 30:279-291.

Venema, F., et al., "Platinum-Catalyzed Oxidation of Aldopentoses to Aldaric Acids,"1992, J. Mol. Catal., 77:75-85.

Wang, T., et al., "Aqueous-Phase Aerobic Oxidation of Alcohols by Soluble Pt Nanoclusters in the Absence of Base," 2007, Chem. Commun., 4375-4377.

Wang T., et al., "Base-free Aqueous-Phase Oxidation of Non-Activated Alcohols with Molecular Oxygen on Soluble Pt Nanoparticles," 2009, Green Chem, 11:562-568.

Besson, M., et al., "Oxidation of Glucose and Gluconate on Pt, Pt Bi, and Pt Au Catalysts," 1996, Recueil des Travaux chimiques des pays-Bas, 115:217-221.

De La Motte, H., "Ueber die Einwirkung von Phosphorpentachlorid und Jodwasserstoffsaure auf Zuckersaure," 1879, Berichte Der Deutschen Chemischen Gesellschaft, 12/2:1571-1573.

Fischer, E., et al., "Ueber eine neue Pentonsaure und die zweite inactive Trioxyglutarsaure," 1891, Berichte Der Deutschen Chemischen Gesellschaft, 24/2:4216-4225.

Tiemann, F., et al., "Ueber Isozuckersaure," 1886, Berichte Der Deutschen Chemischen Gesellschaft, 19/1:1257-1281.

"Roadmap for Biomass Technologies in the United States," Dec. 2002, U.S. Dept. of Energy, 48 pages.

(56) References Cited

OTHER PUBLICATIONS

"Top Value Added for Chemicals from Biomass—vol. 1: Results of Screening for Potential Candidates from Sugars and Synthesis Gas," 2004, Produced by PNNL, NREL and EERE, T. Werpy and G. Petersen, Eds., U.S. Dept. of Energy, 76 pages.

"Acidum Tartaricum (U.S.P.)—Tartaric Acid," 2/42010, Henriette's Herbal Homepage, www.henriettesherbal.com/eclectic/kings/acidum-tart.html, 5 pages.

International Search Report issued in PCT/US2010/038419, dated Jan. 31, 2011, 7 pages.

Written Opinion issued in PCT/US2010/038419, dated Jan. 31, 2011, 14 pages.

International Search Report issued in PCT/US2010/038422, dated Sep. 16, 2010, 6 pages.

Written Opinion issued in PCT/US2010/038422, dated Sep. 16, 2010, 11 pages.

International Search Report issued in PCT/US2010/038408, dated Feb. 2, 2011, 7 pages.

Written Opinion issued in PCT/US2010/038408, dated Feb. 2, 2011, 16 pages.

Gao, S., et al., "Low-Molecular-Weight and Oligomeric Components in Secondary Organic Aerosol from the Ozonolysis of Cycloalkenes and $\alpha$-Pinene," 2004, J Phys Chem A, 108:10147-10164.

Guneral, F., et al., "Age-Related Reference Values for Urinary Organic Acids in a Healthy Turkish Pediatric Population," 1994, Clin Chem, 40(6):862-868.

Pankow, J.F., et al., "Modeling the Formation of Secondary Organic Aerosol. 1. Application of Theoretical Principles to Measurements Obtained in the $\alpha$-Pinene/, $\beta$-Pinene/, Sabinene/, $\Delta$3-Carene/, and Cyclohexene/Ozone Systems," 2001, Environ Sci Technol, 35:1164-1172.

Yang, L., et al., "Photooxidation of Dicarboxylic Acids-Part II: Kinetics, Intermediates and Field Observations," 2008, Atmospheric Environment, 42:868-880.

"Adipic Acid," compounds 24,052-4 and A2,635-7 in Aldrich Handbook of Fine Chemicals and Laboratory Equipment, Nederlands Edition, 2000, p. 40, Sigma-Aldrich, USA.

International Search Report issued in PCT/US2010/060147 dated Apr. 29, 2011, 4 pages.

Written Opinion issued in PCT/US2010/060147 dated Apr. 29, 2011, 10 pages.

Database Caplus Chemical Abstracts Service, Columbus, Ohio, US; Database Accession No. 1987:477541, Abstract of Bitsi et al., Journal of Organometallic Chemistry (1986), 310(1), 115-19.

Kouremenos, K.A., et al., Metabolic Profiling of Infant Urine Using Comprehensive Two-Dimensional Gas Chromatography: Application to the Diagnosis of Organic Acidurias and Biomarker Discovery, 2010, J Chromatography A, 1217:104-111.

Satoh, S., et al., "Electrochemical Reductive Cyclization of Dimethyl Dibromoalkanedioates," 1980, Hok Kaido Dai gaku Kogakubu KenKyu Hokoku, 102:33.

\* cited by examiner

PRODUCTION OF GLUTARIC ACID AND DERIVATIVES FROM CARBOHYDRATE-CONTAINING MATERIALS

REFERENCE TO RELATED APPLICATIONS

This application claims benefit of U.S. provisional application Ser. No. 61/268,414, filed Jun. 13, 2009, the entire disclosure of which is incorporated herein by reference.

FIELD OF THE INVENTION

The present invention generally relates to processes for the chemocatalytic conversion of a pentose source to a glutaric acid product. The present invention includes processes for the conversion of pentose to a glutaric acid product via pentaric acid and/or derivatives thereof. The present invention also includes processes comprising the catalytic oxidation of a pentose to a pentaric acid and catalytic hydrodeoxygenation of pentaric acid and/or derivatives thereof to a glutaric acid product. The present invention also relates to processes for the preparation of industrial chemicals such as diols (e.g., 1,5-pentanediol), diamines (e.g., 1,5-diaminopentane), polyamides and polyesters from a glutaric acid product obtained from processes for the chemocatalytic conversion of a pentose source which includes the catalytic hydrodeoxygenation of a pentaric acid (e.g., xylaric and/or arabinaric acid) and/or derivatives thereof.

BACKGROUND OF THE INVENTION

Hemicelluloses represent the second most abundant carbohydrate in nature, constituting up to approximately 20-35% of lignocellulosic biomass. Hemicelluloses are heterogeneous polymers of pentoses (e.g., xylose and arabinose), hexoses and sugar acids. It is known that hemicelluloses can be acid-hydrolyzed to xylose and subsequently cyclodehydrated to produce furfural. Over 350,000 tonnes of furfural are produced from xylose annually for applications in plastics, pharmaceuticals and agrochemicals. See for example, *Furfural: Hemicelluloses/xylose-derived biochemical*, Mamman et al. Biofuels, Bioprod. Bioref Vol. 2, pp. 438-454.

One of the major challenges for converting biorenewable carbohydrate-derived pentose (e.g., xylose and arabinose derived from hemicellulose) to a broader suite of current commodity and specialty chemicals is the selective removal of oxygen atoms from the carbohydrate. Approaches are known for converting carbon-oxygen single bonds to carbon-hydrogen bonds. See, for example: U.S. Pat. No. 5,516,960; U.S. Patent App. Pub. 2007/0215484 and Japanese Patent No. 78,144,506. Each of these known approaches suffers from various limitations, and we believe that, currently, none of such methods are used industrially for the manufacture of industrial chemicals.

Given the abundance of hemicelluloses, there remains a need for new, industrially scalable methods for the selective and commercially-meaningful conversion of carbon-oxygen single bonds to carbon-hydrogen bonds, especially as applied in connection with the production of chemicals from pentaric acid (and/or derivatives thereof) such as, for example, xylaric acid, and especially for the conversion of pentose (e.g., xylose and arabinose) to valuable chemical intermediates such as glutaric acid, which may be used in the manufacture of diols (e.g., 1,5-pentanediol), diamines (e.g., 1,5-diaminopentane), polyamides, polyesters, polyester polyols, fragrances and pharmaceuticals, among others. See Ullmann's Encyclopedia of Industrial Chemistry, Wiley-VCH 2009 and also U.S. Pat. Nos. 5,290,852, 5,281,647, 4,439,551, WO 2008/144514 and 2008/070762, Japanese Patents 2005060447 and 2001316311, and U.S. Patent App. Pub. 2008/0103232.

SUMMARY OF THE INVENTION

Briefly, therefore, the present invention is directed to processes for preparing a glutaric acid product. In accordance with one embodiment, a process for producing a glutaric acid product from a pentose source is provided. The process comprises converting by chemocatalytic means at least a portion of the pentose source to the glutaric acid product.

In accordance with another embodiment, the process for preparing a glutaric acid product comprises reacting, in the presence of a hydrodeoxygenation catalyst and a halogen source, a C5-backbone substrate and hydrogen to convert at least a portion of the C5-backbone substrate to a glutaric acid product, wherein the C5-backbone substrate comprises a compound of formula I

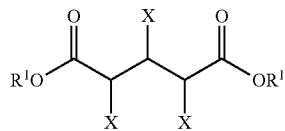

wherein X is independently hydroxyl, oxo, halo, acyloxy, or hydrogen provided that at least one X is not hydrogen and $R^1$ is independently a salt-forming ion, hydrogen, hydrocarbyl, or substituted hydrocarbyl; or a lactone thereof.

In accordance with another embodiment, the process for preparing a glutaric acid product comprises converting at least a portion of a pentose source to a C5-backbone substrate comprising pentaric acid or derivatives thereof, and converting at least a portion of the pentaric acid or derivatives to a glutaric acid product.

The present invention is further directed to processes for preparing pentaric acid. In one embodiment, the process comprises reacting a pentose selected from the group consisting of xylose, arabinose, ribose, lyxose, and mixtures thereof, with oxygen in the presence of an oxidation catalyst and in the substantial absence of added base.

The present invention is further directed to processes for preparing pentaric acid by reacting pentose with oxygen in the presence of an oxidation catalyst, wherein at least a portion of the pentose is solubilized with a weak carboxylic acid, preferably acetic acid.

The present invention is further directed to processes for the preparation of industrial chemicals such as diols (e.g., 1,5-pentanediol) diamines (e.g., 1,5-diaminopentane), polyamides and polyesters, among others, from a glutaric acid product obtained from processes comprising the chemocatalytic conversion of a pentose source to a C5-backbone substrate, and the catalytic hydrodeoxygenation of a C5-backbone substrate (e.g., xylaric and/or arabinaric acid and/or derivatives thereof) to a glutaric acid product.

The present invention is further directed to glutaric acid product, diols, diamines, polyamides and polyesters produced at least in part from a process comprising the hydrodeoxygenation of a C5-backbone substrate and, more particularly, xylaric acid and/or derivatives thereof.

Other objects and features will become apparent and/or will be pointed out hereinafter.

DESCRIPTION OF THE PREFERRED EMBODIMENTS

In accordance with the present invention, applicants disclose processes for the chemocatalytic conversion of a pentose source to a glutaric acid product.

Further, in accordance with the present invention, applicants disclose processes for the catalytic hydrodeoxygenation of a C5-backbone substrate to a glutaric acid product. The catalytic hydrodeoxygenation includes reacting, in the presence of a hydrodeoxygenation catalyst (i.e., catalyst suitable for the hydrodeoxygenation reaction) and a halogen source, a C5-backbone substrate and hydrogen to convert at least a portion of the C5-backbone substrate to a glutaric acid product. The hydrodeoxygenation catalyst of the present invention comprises a d-block metal (i.e., transition metal; groups 3-12 of the periodic table) that is hydroxyl, halo, oxo or acyloxy selective, more typically hydroxyl-selective, which increases yield and improves process economics.

The present invention also relates to processes for the catalytic production of pentaric acid and/or derivatives thereof from a pentose selected from the group consisting of xylose, arabinose, ribose, lyxose, and mixtures thereof. The process includes reacting the pentose with oxygen (wherein the oxygen is supplied to the reaction as air, oxygen-enriched air, oxygen alone, or oxygen with one or more other constituents substantially inert to the reaction) in the presence of an oxidation catalyst and in the substantial absence of added base. Conducting the oxidation reaction in the substantial absence of added base facilitates product recovery and improves process economics. Further, this reaction may be conducted in the presence of a weak carboxylic acid, such as acetic acid, in which at least a portion of the pentose is solubilized.

In another aspect of the invention, a glutaric acid product prepared in accordance with the disclosed processes may be converted, according to processes known in the art, to various other industrially significant chemicals including, for example, diols (e.g., 1,5-pentanediol), diamines (e.g., 1,5-diaminopentane), polyamides and polyesters among others. Thus diols (e.g., 1,5-pentanediol), diamines (e.g., 1,5-diaminopentane) polyamides and polyesters, among others, may be prepared from pentoses derived from biorenewable sources containing hemicellulose.

I. Feedstocks

Pentoses are sugars containing five carbons and generally include xylose, arabinose, ribose, and lyxose. Pentoses can be obtained from various carbohydrate-containing sources (particularly hemicellulose-containing sources) including biorenewable sources such as energy crops, plant biomass, agricultural wastes, forestry residues, sugar processing residues and plant-derived household wastes. More generally, biorenewable sources that may be used in accordance with the present invention include any renewable organic matter that includes a source of hemicellulose such as, for example, switch grass, straw (e.g., rice straw, barley straw, wheat straw, rye straw, oat straw), oat hulls, miscanthus, cassava, trees (hardwood and softwood), vegetation, and crop residues (e.g., bagasse and corn stover). Other sources can include, for example, waste materials (e.g., spent paper, green waste, municipal waste, etc.). Pentoses may be isolated from biorenewable sources containing hemicelluloses using methods that are known in the art. Furthermore, methods to convert pentoses to a limited suite of chemicals are also known in the art. For illustrations of these methods, see, for example, Saha, J. Ind. Microbiol. Biotechnol. vol. 30, pp. 279-291 (2003), and Kamm, Gruber and Kamm, Biorefineries-Industrial Processes and Products, Wiley-VCH, Weinheim 2006.

II. Preparation of a Pentaric Acid

In accordance with the present invention, pentose selected from the group consisting of xylose, arabinose, ribose, lyxose, and mixtures thereof, is converted to pentaric acid and/or derivatives thereof. The preparation of various pentaric acids (pentaric acids include xylaric, arabinaric, ribaric and lyxaric) can be accomplished from pentoses using oxidation methods that are generally known in the art. See, for example, Journal of Molecular Catalysis, Vol. 77, pp. 75-85 (1992), which illustrates a method for the preparation of pentaric acids from aldopentoses using a platinum catalyst in the presence of oxygen and a base. Other oxidation methods may also be employed, see for example, U.S. Pat. Nos. 6,049,004, 5,599,977, and 6,498,269, and U.S. Patent App. Pub. No. 2008/033205. Similarly, U.S. Pat. No. 5,731,467 discloses method of producing xylaric acid by the oxidative degradation of 5-ketogluconic acid or a salt thereof in alkaline medium using oxygen. However, these processes suffer from economic shortcomings resulting from, among other matters, process yield limitations and the requirement for additional reaction constituents.

Applicants have discovered that pentose (i.e., an oxidation substrate) selected from the group consisting of xylose, arabinose, ribose, lyxose, and mixtures thereof, may be converted to pentaric acid in high yield by reacting the oxidation substrate with oxygen (wherein the oxygen is supplied to the reaction as air, oxygen-enriched air, oxygen alone, or oxygen with one or more other constituents substantially inert to the reaction) in the presence of an oxidation catalyst and in the absence of added base according to the following reaction:

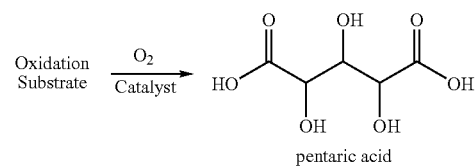 [SMILES: "O2" ; O=C(O)C(O)C(O)C(O)C(=O)O]

pentaric acid

Surprisingly, conducting the oxidation reaction in the absence of added base and in accordance with the reaction conditions set forth herein, does not lead to significant catalyst poisoning effects and catalyst oxidation activity is maintained. The absence of added base advantageously facilitates separation and isolation of pentaric acid, thereby providing a process that is more amenable to industrial application, and improves overall process economics by eliminating a reaction constituent. The "absence of added base" as used herein means that base, if present (for example, as a constituent of a feedstock), is present in a concentration which has essentially no effect on the efficacy of the reaction; i.e., the oxidation reaction is being conducted essentially free of added base. It has been further discovered that conducting the oxidation reaction under increased oxygen partial pressures and/or higher oxidation reaction mixture temperatures tends to increase the yield of pentaric acid when the reaction is conducted in the substantial absence of added base. It has also been discovered that this oxidation reaction can be carried out in the presence of a weak carboxylic acid, such as acetic acid, in which pentose is soluble. The term "weak carboxylic acid" as used herein means any unsubstituted or substituted carboxylic acid having a pKa of at least about 3.5, more preferably at least about 4.5, and more particularly unsubstituted acids such as acetic acid, propionic acid or butyric acid, or mixtures thereof.

In these and various other embodiments, the initial pH of the reaction mixture is no greater than about 7, and typically less than 7 such, for example, 6 or less when a weak carboxylic acid is used to solubilize at least a portion of the pentose. In accordance with the present invention, the initial pH of the reaction mixture is the pH of the reaction mixture prior to contact with oxygen in the presence of an oxidation catalyst. It is expected that the pH of the reaction mixture after oxygen contact will vary as the reaction proceeds. It is believed that as the concentration of pentaric acid increases (as the reaction proceeds) the pH will decrease from the initial pH.

Another advantage of the present invention is the essential absence of nitrogen as an active reaction constituent. Typically, nitrogen is employed in known processes as an oxidant such as in the form of nitrate, in many instances as nitric acid. The use of nitrogen in a form in which it is an active reaction constituent, such as nitrate or nitric acid, results in the need for $NO_x$ abatement technology and acid regeneration technology, both of which add significant cost to the production of pentaric acid from these known processes, as well as providing a corrosive environment which may deleteriously affect the equipment used to carry out the process. By contrast, for example, in the event air or oxygen-enriched air is used in the oxidation reaction of the present invention as the source of oxygen, the nitrogen is essentially an inactive or inert constituent. Thus, for example, in accordance with the present invention, an oxidation reaction employing air or oxygen-enriched air is a reaction conducted essentially free of nitrogen in a form in which it would be an active reaction constituent.

In various embodiments, the pentose is selected from the group consisting of xylose, arabinose, and mixtures thereof. In these and other embodiments, the pentose is converted to a pentaric acid selected from the group consisting of xylaric acid, arabinaric acid, and mixtures thereof.

Generally, the temperature of the oxidation reaction mixture is at least about 40° C., more typically 60° C. or higher. In various embodiments, the temperature of the oxidation reaction mixture is from about 40° C. to about 150° C., from about 60° C. to about 150° C., from about 70° C. to about 150° C., or from about 70° C. to about 140° C., or from about 80° C. to about 120° C.

Typically, the partial pressure of oxygen is at least about 15 pounds per square inch absolute (psia) (104 kPa), at least about 25 psia (172 kPa), at least about 40 psia (276 kPa), at least about 60 psia (414 kPa). In various embodiments, the partial pressure of oxygen is up to about 1000 psia (6895 kPa) or, more typically, in the range of from about 15 psia (104 kPa) to about 500 psia (3447 kPa).

The oxidation reaction is typically conducted in the presence of a solvent to pentose. Solvents suitable for the oxidation reaction include water and weak carboxylic acids such as acetic acid. Utilization of weak carboxylic acid as a solvent adds cost to the process which cost, as a practical matter, must be balanced against any benefits derived from the use thereof. Thus, suitable solvents for the present invention include water, mixtures of water and weak carboxylic acid, or weak carboxylic acid.

In general, the oxidation reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design*, Couper et al., Elsevier 1990, which is incorporated herein by reference. It should be understood that the pentose(s), oxygen, any solvent, and the oxidation catalyst may be introduced into a suitable reactor separately or in various combinations.

Catalysts suitable for the oxidation reaction ("oxidation catalyst") include heterogeneous catalysts, including solid-phase catalysts comprising one or more supported or unsupported metals. In various embodiments, metal is present at a surface of a support (i.e., at one or more surfaces, external or internal). Typically, metal is selected from the group consisting of palladium, platinum, and combinations thereof. Additional other metals may be present, including one or more d-block metals, alone or in combination with one or more rare earth metals (e.g. lanthanides), or alone or in combination with one or more main group metals (e.g. Al, Ga, Tl, In, Sn, Pb or Bi). In general, the metals may be present in various forms (e.g., elemental, metal oxide, metal hydroxides, metal ions, etc.). Typically, the metal(s) at a surface of a support constitute from about 0.25% to about 10%, or from about 1% to about 8%, or from about 2.5% to about 7.5% (e.g., 5%) of the total weight of the catalyst.

In various embodiments, the oxidation catalyst comprises a first metal (M1) and a second metal (M2) at a surface of a support, wherein the M1 metal is selected from the group consisting of palladium and platinum and the M2 metal is selected from the group consisting of d-block metals, rare earth metals, and main group metals, wherein the M1 metal is not the same metal as the M2 metal. In various preferred embodiments, the M1 metal is platinum and the M2 metal is selected from the group consisting of manganese, iron, and cobalt.

The M1:M2 molar ratio may vary, for example, from about 500:1 to about 1:1, from about 250:1 to about 1:1, from about 100:1 to about 1:1, from about 50:1 to about 1:1, from about 20:1 to about 1:1, or from about 10:1 to about 1:1. In various other embodiments, the M1:M2 molar ratio may vary, for example, from about 1:100 to about 1:1, from about 1:50 to about 1:1, from about 1:10 to about 1:1, from about 1:5 to about 1:1, or from about 1:2 to about 1:1.

Moreover, the weight percents of M1 and M2 relative to the catalyst weight may vary. Typically, the weight percent of M1 may range from about 0.5% to about 10%, more preferably from about 1% to about 8%, and still more preferably from about 2.5% to about 7.5% (e.g., about 5%). The weight percent of M2 may range from about 0.25% to about 10%, from about 0.5% to about 8%, or from about 0.5% to about 5%.

In various other embodiments, a third metal (M3) may be added to produce a M1/M2/M3 catalyst wherein the M3 metal is not the same metal as the M1 metal and the M2 metal. In other embodiments a fourth metal (M4) may be added to produce a M1/M2/M3/M4 catalyst wherein the M4 metal is not the same metal as the M1 metal, the M2 metal, or the M3 metal. The M3 metal and M4 metal may each be selected from the group consisting of d-block metals, rare earth metals (e.g. lanthanides), or main group metals (e.g. Al, Ga, Tl, In, Sn, Pb or Bi).

Suitable catalyst supports include carbon, alumina, silica, ceria, titania, zirconia, niobia, zeolite, magnesia, clays, iron oxide, silicon carbide, aluminosilicates, and modifications, mixtures or combinations thereof. The support materials may be modified using methods known in the art such as heat treatment, acid treatment or by the introduction of a dopant (for example, metal-doped titanias, metal-doped zirconias (e.g., tungstated-zirconia), metal-doped cerias, and metal-modified niobias). Preferred supports are carbon (which may be activated carbon, carbon black, coke or charcoal), alumina, and silica. In various embodiments, the support of the oxidation catalyst is selected from the group consisting of carbon, alumina, and silica.

When a catalyst support is used, the metals may be deposited using procedures known in the art including, but not limited to, incipient wetness, ion-exchange, deposition-precipitation, and vacuum impregnation. When two or more metals are deposited on the same support, they may be deposited sequentially or simultaneously. In various embodiments, following metal deposition, the catalyst is dried at a temperature of at least about 50° C., more typically at least about 120° C. for a period of time of about 1 hour, more typically 3 hours or more. In these and other embodiments, the catalyst is dried under sub-atmospheric pressure conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of at least about 500° C. for a period of time (e.g., at least about 3 hours).

The pentaric acid produced in accordance with the above may be converted to various other pentaric acid derivatives, such as salts, esters, ketones, and lactones. Methods to convert carboxylic acids to such derivatives are known in the art, see, for example, Wade, *Organic Chemistry* 3$^{rd}$ ed, Prentice Hall 1995.

III. Preparation of a Glutaric Acid Product

In accordance with the present invention, a glutaric acid product may be prepared by chemocatalytic conversion of a pentose source. In various embodiments, preparation of a glutaric acid product includes chemocatalytic conversion of a pentose source to pentaric acid. In these and other embodiments, a C5-backbone substrate comprising at least a portion of the pentaric acid or derivatives thereof is converted to a glutaric acid product. Derivatives of pentaric acids include compounds as defined below.

The C5-backbone substrate comprises a compound of the formula I:

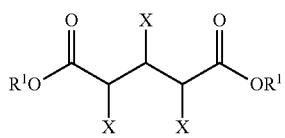

wherein X is independently hydroxyl, oxo, halo, acyloxy, or hydrogen provided that at least one X is not hydrogen and $R^1$ is independently a salt-forming ion, hydrogen, hydrocarbyl, or substituted hydrocarbyl; or a lactone thereof.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl, substituted cycloalkyl and the like.

Salt forming ions include, without limitation, for example ammonium ions and metal ions (e.g., alkali and alkaline earth metals). When $R^1$ is a salt forming ion (i.e., a cation), the carboxyl group may be considered to be anion (i.e., carboxylate anion).

In various embodiments, the C5-backbone substrate comprises a compound of formula I, wherein X is independently hydroxyl, oxo, halo, $C_1$-$C_6$ acyloxy, or hydrogen provided that at least one X is not hydrogen. In other embodiments, the C5-backbone substrate comprises a compound of formula I, wherein X is hydroxyl and $R^1$ is independently a salt-forming ion, hydrogen, hydrocarbyl, or substituted hydrocarbyl.

As shown in formula I, the C5-backbone substrate contains a five carbon chain comprising three chiral centers. As a result several stereoisomers are possible. In various embodiments, the preferred C5-backbone substrate comprises a pentaric acid selected from the group consisting of xylaric acid, arabinaric acid, and mixtures thereof.

The C5-backbone substrate may also include various ketones. For example, not wishing to be bound by theory, when pentaric acids are further oxidized, ketones such as an α-keto-xylaric acid (2,3-dihydroxy-4-oxopentanedioic acid) and various stereoisomers thereof, may be formed.

The C5-backbone substrate may comprise various lactones derived from pentaric acids. For example, not wishing to be bound by theory, it is believed that various monolactones may be present in equilibrium with various pentaric acids in aqueous solution, including for example, xylaro-5,2-lactone, arabinaro-5,2-lactone, ribaro-5,2-lactone, and lyxaro-5,2-lactone or stereoisomers thereof. Moreover, processes have been developed to quantitatively convert pentaric acids or a salt thereof in solution to one or more lactones and recover a substantially pure lactone stream. See, for example, U.S. Patent App. Pub. Nos. 2006/0084817 and 2006/0084800.

In accordance with the present invention, a glutaric acid product (formula II) may be prepared by reacting, in the presence of a hydrodeoxygenation catalyst and a halogen source a C5-backbone substrate (formula I) and hydrogen (it being understood that hydrogen means essentially hydrogen or hydrogen in combination with other constituents that are essentially inert to the reaction), according to the following reaction:

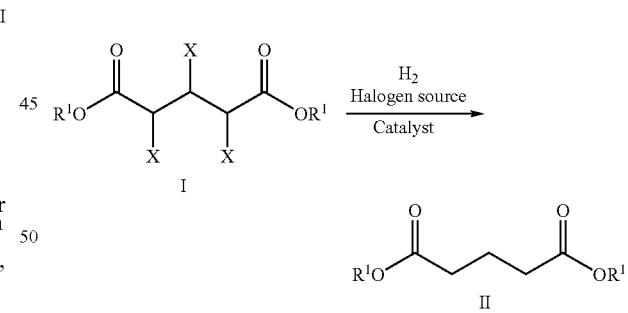

wherein X and $R^1$ are defined as described above.

In preferred embodiments, the glutaric acid product (formula II) comprises glutaric acid.

In the above reaction, a C5-backbone substrate is converted to a glutaric acid product by catalytic hydrodeoxygenation in which carbon-hydroxyl groups are converted to carbon-hydrogen groups. In various embodiments, the catalytic hydrodeoxygenation is hydroxyl-selective wherein the reaction is completed without substantial conversion of the one or more other non-hydroxyl functional group of the substrate.

In accordance with the present invention, a C5-backbone substrate is catalytically hydrodeoxygenated in the presence of hydrogen, a halogen source and a hydrodeoxygenation catalyst. Without being bound by theory, it is believed that during this reaction the C5-backbone substrate is halogenated with the halogen source, to form a halogenated intermediate containing a carbon-halogen bond (e.g., a secondary alcohol group on the pentaric acid is converted to a halide to produce an alkyl halide). The carbon-halogen bond of the halogenated intermediate is believed to be converted to a carbon-hydrogen bond via one or more of the following pathways. In the first pathway, the halogenated intermediate reacts with hydrogen in the presence of the hydrodeoxygenation catalyst leading to the formation of a carbon-hydrogen bond along with the generation of hydrohalic acid. In the second pathway, the halogenated intermediate undergoes a dehydrohalogenation reaction to form an olefin intermediate and hydrohalic acid. The olefin is further reduced in the presence of the hydrodeoxygenation catalyst leading to the formation of a carbon-hydrogen bond (or the olefin may be an enol form of a ketone which can interconvert to a keto form which can reduce to an alcohol group which can undergo further hydrodeoxygenation). Effecting the reaction pursuant to the above described first and second pathways generates hydrohalic acid as a by-product, which is available for further reaction. In the third pathway, the halogenated intermediate reacts with hydrohalic acid leading to the formation of a carbon-hydrogen bond along with the formation of molecular halogen (or interhalogen). Effecting the reaction pursuant to the third pathway generates molecular halogen as a by-product, which is available for further reaction. One or more of the various pathways described above may occur concurrently.

It should be recognized that the hydrodeoxygenation reaction can be conducted by first forming and optionally purifying or isolating these various intermediates formed by combining a C5-backbone substrate and a halogen source and subsequently reacting the intermediate with hydrogen in the presence of the hydrodeoxygenation catalyst and optionally in the absence of any additional halogen source.

In various embodiments, the C5-backbone substrate is halogenated with hydrohalic acid to form a halogenated intermediate (e.g., an alkyl halide). In other embodiments, the C5-backbone substrate is halogenated with a molecular halogen to form the halogenated intermediate (e.g., an alkyl halide).

The halogen source may be in a form selected from the group consisting of atomic, ionic, molecular, and mixtures thereof. Halogen sources include hydrohalic acids (e.g., HBr, HI, HCl and mixtures thereof; preferably HBr and/or HI); halide salts; (substituted or unsubstituted) alkyl halides; or elemental chlorine, bromine or iodine or mixtures thereof (preferably bromine and/or iodine). In various embodiments the halogen source is in molecular form and, more preferably, is bromine or iodine. In more preferred embodiments, the halogen source is a hydrohalic acid, in particular hydrogen bromide or hydrogen iodide.

Generally, the molar ratio of halogen to the C5-backbone substrate is equal to or less than about 1. In various embodiments, the mole ratio of halogen to the C5-backbone substrate is typically from about 0.1:1 to about 1:1, more typically from about 0.3:1 to about 0.7:1, and still more typically about 0.5:1.

Generally, the reaction allows for recovery of the halogen source and catalytic quantities (where molar ratio of halogen to the C5-backbone substrate is less than about 1) of halogen can be used, recovered, and recycled for continued use as a halogen source.

Generally, the temperature of the hydrodeoxygenation reaction mixture is at least about 80° C., more typically at least about 100° C. In various embodiments, the temperature of the hydrodeoxygenation reaction mixture is from about 80° C. to about 250° C., more preferably from about 100° C. to about 200° C., and still more preferably from about 120° C. to about 180° C.

Typically, the partial pressure of hydrogen is at least about 25 psia (172 kPa), more typically, at least about 200 psia (1379 kPa), or at least about 400 psia (2758 kPa). In various embodiments, the partial pressure of hydrogen is from about 25 psia (172 kPa) to about 2500 psia (17237 kPa), from about 200 psia (1379 kPa) to about 2000 psia (13,790 kPa), or from about 400 psia (2758 kPa) to about 1500 psia (10,343 kPa).

The hydrodeoxygenation reaction is typically conducted in the presence of a solvent. Solvents suitable for the selective hydrodeoxygenation reaction include water and carboxylic acids, amides, esters, lactones, sulfoxides, sulfones, and mixtures thereof. Preferred solvents include water, mixtures of water and weak carboxylic acid, and weak carboxylic acid. A preferred weak carboxylic acid is acetic acid.

In general, the reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design*, Couper et al., Elsevier 1990, which is incorporated herein by reference. It should be understood that the C5-backbone substrate, halogen source, hydrogen, any solvent, and the hydrodeoxygenation catalyst may be introduced into a suitable reactor separately or in various combinations.

In various embodiments, the hydrodeoxygenation catalyst is heterogeneous, but suitable homogeneous catalyst may be employed. In these and various other preferred embodiments the hydrodeoxygenation catalyst comprises a solid-phase heterogeneous catalyst in which one or more metals is present at a surface of a support (i.e., at one or more surfaces, external or internal). Preferred metals are d-block metals which may be used alone, in combination with each other, in combination with one or more rare earth metals (e.g. lanthanides), or in combination with one or more main group metals (e.g., Al, Ga, Tl, In, Sn, Pb or Bi). Preferred d-block metals are selected from the group consisting of cobalt, nickel, ruthenium, rhodium, palladium, osmium, iridium, platinum, and combinations thereof. More preferred d-block metals are selected from the group consisting of ruthenium, rhodium, palladium, platinum, and combinations thereof. In general, the metals may be present in various forms (e.g., elemental, metal oxide, metal hydroxides, metal ions etc.). Typically, the metal(s) at a surface of a support may constitute from about 0.25% to about 10%, or from about 1% to about 8%, or from about 2.5% to about 7.5% (e.g., 5%) of the catalyst weight.

In various embodiments, the catalyst comprises two or more metals. For example, two of more metals (M1 and M2) may be co-supported on or within the same support (e.g., as a mixed-metal catalyst on silica; M1/M2/Silica catalyst), or they may be supported on different support materials. In various embodiments the hydrodeoxygenation catalyst comprises a first metal (M1) and a second metal (M2) at a surface of a support, wherein the M1 metal comprises a d-block metal and the M2 metal is selected from the group consisting of d-block metals, rare earth metals, and main group metals, wherein the M1 metal is not the same metal as the M2 metal. In various preferred embodiments, the M1 metal is selected from the group consisting of ruthenium, rhodium, palladium, and platinum. In various embodiments, the M2 metal is selected from the group consisting of titanium, vanadium, chromium, manganese, iron, cobalt, nickel, copper, molybdenum, ruthenium, rhodium, palladium, silver, tungsten, iridium, platinum, and gold. In more preferred embodiments, the M2 metal is selected from the group consisting of molybdenum, ruthenium, rhodium, palladium, iridium, platinum, and gold.

In more preferred embodiments, the M1 metal is selected from the group of platinum, rhodium and palladium and the M2 metal is selected from the group consisting of ruthenium, rhodium, palladium, iridium, platinum, and gold.

In various embodiments, the M1:M2 molar ratio may vary, for example, from about 500:1 to about 1:1, from about 250:1 to about 1:1, from about 100:1 to about 1:1, from about 50:1 to about 1:1, from about 20:1 to about 1:1, or from about 10:1 to about 1:1. In various other embodiments, the M1:M2 molar ratio may vary, for example, from about 1:100 to about 1:1, from about 1:50 to about 1:1, from about 1:10 to about 1:1, from about 1:5 to about 1:1, or from about 1:2 to about 1:1.

Moreover, in various embodiments, the weight percents of M1 and M2 relative to the total catalyst weight may vary. Typically, the weight percent of M1 may range from about 0.5% to about 10%, more preferably from about 1% to about 8%, and still more preferably from about 2.5% to about 7.5% (e.g., about 5%). The weight percent of M2 may range from about 0.25% to about 10%, from about 0.5% to about 8%, or from about 0.5% to about 5%.

In various other embodiments, a third metal (M3) may be added to produce a M1/M2/M3 catalyst wherein the M3 metal is not the same metal as the M1 metal and the M2 metal. In other embodiments, a fourth metal (M4) may be added to produce a M1/M2/M3/M4 catalyst wherein the M4 metal is not the same metal as the M1 metal, the M2 metal or the M3 metal. The M3 metal and M4 metal may each be selected from the group consisting of d-block metals, rare earth metals (e.g. lanthanides), or main group metals (e.g. Al, Ga, Tl, In, Sn, Pb or Bi).

Preferred catalyst supports include carbon, alumina, silica, ceria, titania, zirconia, niobia, zeolite, magnesia, clays, iron oxide, silicon carbide, aluminosilicates, and modifications, mixtures or combinations thereof. The supports may be modified through methods known in the art such as heat treatment, acid treatment, the introduction of a dopant (for example, metal-doped titanias, metal-doped zirconias (e.g. tungstated zirconia), metal-doped cerias, and metal-modified niobias). In various preferred embodiments, the hydrodeoxygenation catalyst support is selected from the group consisting of silica or titania.

When a catalyst support is used, the metals may be deposited using procedures known in the art including, but not limited to, incipient wetness, ion-exchange, deposition-precipitation and vacuum impregnation. When the two or more metals are deposited on the same support, they may be deposited sequentially or simultaneously. In various embodiments, following metal deposition, the catalyst is dried at a temperature of at least about 50° C., more preferably at least about 120° C. for a period of time of at least about 1 hour, more typically at least about 3 hours, or more. In these and other embodiments, the catalyst is dried under sub-atmospheric pressure conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of at least about 500° C. for a period of time (e.g., at least about 3 hours).

Without being bound by theory not expressly recited in the claims, catalysts mixtures (co-catalysts or mixed metal catalysts) containing more than one metal may affect separate steps of the mechanistic reaction pathway.

A glutaric acid product may be recovered from the hydrodeoxygenation reaction mixture by one or more conventional methods known in the art including, for example, solvent extraction, crystallization, or evaporative processes.

IV. Downstream Chemical Products

Various methods are known in the art for conversion of glutaric acid to downstream chemical products or intermediates including diols (e.g., 1,5-pentanediol), diamines (e.g., 1,5-diaminopentane), polyamides and polyesters, among others. See, for example Ullmann's Encyclopedia of Industrial Chemistry, Wiley-VCH 2009, and also U.S. Pat. Nos. 5,290,852, 5,281,647, 4,439,551, WO 2008/144514 and 2008/070762, JP 2005060447, JP 2001316311, US Patent Appl. 20080103232.

In various embodiments, a glutaric acid product is converted to 1,5-pentanediol wherein the glutaric acid product is prepared in accordance with the present invention. 1,5-pentanediol is a specialty chemical intermediate used in the production of various polymers and plasticizers. See, for example, JP 2001316311.

In other embodiments, a glutaric acid product is converted to 1,5-diaminopentane, wherein the glutaric acid product is prepared in accordance with the present invention. 1,5-diaminopentane can be used in the production of polyamides. See, for example, JP 2005060447.

In other embodiments, a glutaric acid product is converted to a polyester, wherein the glutaric acid product is prepared in accordance with the present invention.

Moreover, various methods are known in the art for conversion of xylaric acid to downstream chemical products such as polyhydroxypolyamide polymers. See, for example, U.S. Pat. No. 4,833,230. Therefore, in various embodiments, xylaric acid is reacted with polymer precursors to form a polyhydroxypolyamide polymer, wherein the xylaric acid is prepared in accordance with the present invention.

When introducing elements of the present invention or the preferred embodiments(s) thereof, the articles "a", "an", "the" and "said" are intended to mean that there are one or more of the elements. The terms "comprising", "including", "containing" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

Reactions were conducted in 1 mL glass vials housed in a pressurized vessel in accordance with the procedures described in the examples below. Product yields were determined using a Dionex ICS-3000 Chromatography system. For Example 1, the products were first separated on an Ionpac® ASII-HC column and then quantified by conductivity detection through comparison with calibration standards. For Example 2, the products were first separated on an Acclaim®

Organic Acid column and then quantified by an ICS-Series PDA-1 UV Detector through comparison with calibration standards.

Example 1

Oxidation of Xylose, Ribose and Arabinose

Preparation of 4 wt. % Pt/Silica Catalysts

Multiple portions of suitably concentrated aqueous Pt(NO$_3$)$_2$ solutions (Heraeus) were added to the appropriate support (wherein the total combined volume of the Pt(NO$_3$)$_2$ solutions was matched to equal to the pore volume of the silica support) with agitation between additions. Post impregnation, the product was dried in a furnace at 120° C. for 12 hours. Material for catalyst testing was prepared by reduction under flowing 5 vol. % H$_2$ in N$_2$ for 3 hours at 200° C.

Oxidation Reactions

Catalysts were dispensed into 1 mL vials within a 96-well reactor insert (Symyx Solutions). The reaction substrates were aqueous solutions of D-(+)-Xylose, D-(−)-Ribose, and D-(−)-Arabinose (all Acros Organics). To each vial was added 250 µL of substrate solution. The vials were each covered with a Teflon pin-hole sheet, a silicone pin-hole mat and steel gas diffusion plate (Symyx Solutions). The reactor insert was placed in a pressure vessel and charged three times with oxygen to 100 psig with venting after each pressurization step. The reactor was then charged to 75 psig with oxygen, closed, and placed on a shaker and heated at 90° C. for 8 hours. After the reaction time had elapsed shaking was stopped and the reactor cooled to room temperature whereupon the reactors were vented. Samples for ion-chromatography (IC) analysis were prepared by adding to each reaction vial 750 µL of water then the plate was covered and mixed followed by centrifugation to separate catalyst particles. Each reaction sample was further diluted by performing two 16-fold dilutions with 100 µL 50 ppm HCl solution added as internal standard during the second serial dilution step. The results are presented in Table 1.

TABLE 1

Oxidation Reactions with 4 wt. % Pt catalysts

| Example | Substrate | Substrate concentration/ mM | Catalyst support | Catalyst mass/ mg | Pentaric acid yield/% |
| --- | --- | --- | --- | --- | --- |
| 1 | Xylose | 552 | Silica Cariact G-6 5 µm | 8 | 29 |
| 2 | Xylose | 552 | Silica Merck 10180 | 8 | 14 |
| 3 | Xylose | 552 | Silica Davisil 635 | 8 | 18 |
| 4 | Ribose | 552 | Silica Cariact G-6 5 µm | 9 | 52 |
| 5 | Ribose | 552 | Silica Merck 10180 | 8 | 38 |
| 6 | Ribose | 552 | Silica Davisil 635 | 8 | 44 |
| 7 | Arabinose | 552 | Silica Cariact G-6 5 µm | 8 | 46 |
| 8 | Arabinose | 552 | Silica Merck 10180 | 8 | 34 |
| 9 | Arabinose | 552 | Silica Davisil 635 | 8 | 35 |

Example 2

Xylaric Acid to Glutaric Acid

Preparation of M1/Silica Catalysts (M1=Rh, Pd, Pt).

2 g of dried 5 µm Silica Cariact (Fuji Silysia) was weighed into vials. Suitably concentrated M1 stock solutions (M1=Rh, Pd, Pt) were prepared from concentrated acidic stock solutions purchased from Heraeus (see Table 1). For each M1, multiple additions of the dilute M1 stock solution were added to the support (Silica pore volume=0.7 mL/g) until a total volume of 1.4 ml was reached. After each addition, the mixtures were agitated to impregnate the support. Post impregnation, the 5 wt. % M1/Support mixtures were dried in a furnace at 120° C. for 12 hours, followed by calcination at 500° C. or 3 hours. Upon cooling the catalysts were stored in a dessicator until used.

Xylaric Acid to Glutaric Acid Reactions.

The arrays of catalysts were transferred to 1 mL glass vials within a 96-well reactor insert (Symyx Solutions). Each vial within each array received a glass bead and 250 µL of 0.2 M Xylaric Acid 0.1 to 0.3 M of either HBr (in Acetic Acid, Sigma-Aldrich) or HI (Sigma-Aldrich). Upon solution addition, the arrays of vials were covered with a Teflon pin-hole sheet, a silicone pin-hole mat and steel gas diffusion plate (Symyx Solutions). The reactor insert was placed in a pressure vessel, pressurized and vented 3 times with nitrogen and 3 times with hydrogen before being pressurized with hydrogen to 710 psig, heated to 140° C. and shaken for 3 hours. After 3 hours the reactors were cooled, vented and purged with nitrogen. 750 μl of water was then added to each vial. Following the water addition, the arrays were covered and shaken to ensure adequate mixing. Subsequently, the covered arrays were placed in a centrifuge to separate the catalyst particles. Each reaction samples was then diluted 2-fold with water to generate a sample for analysis by HPLC. The results are presented in Table 2.

TABLE 2

| Example Number | Catalyst (wt. % M1/Support) | M1 Precursor | Halide Source | Halide Concentration (M) | Catalyst Amount (mg) | Glutaric Acid Yield (%) |
|---|---|---|---|---|---|---|
| 1 | 5% Rh/Silica 5 μm Cariact | Rh(NO$_3$)$_3$ | HBr | 0.3 | 8 | 41 |
| 2 | 5% Rh/Silica 5 μm Cariact | Rh(NO$_3$)$_3$ | HBr | 0.2 | 8 | 39 |
| 3 | 5% Pt/Silica 5 μm Cariact | Pt(NO$_3$)$_2$ | HI | 0.2 | 8 | 35 |
| 4 | 5% Rh/Silica 5 μm Cariact | Rh(NO$_3$)$_3$ | HI | 0.1 | 8 | 37 |
| 5 | 5% Pt/Silica 5 μm Cariact | Pt(NO$_3$)$_2$ | HI | 0.1 | 8 | 31 |
| 6 | 5% Pd/Silica 5 μm Cariact | Pd(NO$_3$)$_2$ | HBr | 0.1 | 8 | 39 |
| 7 | 5% Rh/Silica 5 μm Cariact | Rh(NO$_3$)$_3$ | HBr | 0.1 | 8 | 24 |

What is claimed is:

1. A process for preparing a glutaric acid product, the process comprising:
reacting, in the presence of a heterogeneous hydrodeoxygenation catalyst comprising at least one d-block metal selected from the group consisting of Co, Ni, Ru, Rh, Pd, Os, Ir, Pt, and combinations thereof at a surface of a support and a halogen source, a C5-backbone substrate and hydrogen to convert at least a portion of the C5-backbone substrate to a glutaric acid product, wherein the C5-backbone substrate comprises a compound of formula I

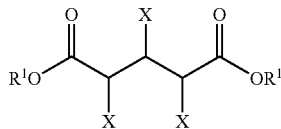

I wherein X is independently hydroxyl, oxo, halo, acyloxy or hydrogen provided that at least one X is not hydrogen and R$^1$ is independently a salt-forming ion, hydrogen, hydrocarbyl, substituted hydrocarbyl, or lactone thereof and the glutaric acid product comprises a compound of formula II

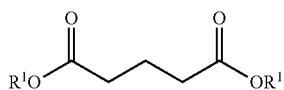

II wherein R$^1$ is as defined for formula I.

2. The process as set forth in claim 1 wherein the C5-backbone substrate comprises a compound of formula I, wherein X is hydroxyl and R$^1$ is independently a salt-forming ion, hydrogen, hydrocarbyl, or substituted hydrocarbyl.

3. The process as set forth in claim 1 wherein the C5-backbone substrate comprises a pentaric acid.

4. The process as set forth in claim 1 wherein the C5-backbone substrate comprises a chemical selected from the group consisting of xylaric acid, arabinaric acid, derivatives of such acids, and mixtures thereof.

5. The process as set forth in claim 3 wherein the pentaric acid comprises an acid selected from the group consisting of xylaric and arabinaric acid.

6. The process as set forth in claim 4 wherein at least a portion of the C5-backbone substrate is solubilized with a weak carboxylic acid.

7. The process as set forth in claim 6 wherein the weak carboxylic acid is acetic acid.

8. The process as set forth in claim 1 wherein the d-block metal is selected from the group consisting of Ru, Rh, Pd, Pt, and combinations thereof.

9. The process as set forth in claim 1 wherein the hydrodeoxygenation catalyst comprises a first metal and a second metal, wherein the first metal is selected from the group consisting of Ru, Rh, Pd, Pt, and combinations thereof, and the second metal is selected from the group consisting of Mo, Ru, Rh, Pd, Ir, Pt, and Au, and wherein the second metal is not the same as the first metal.

10. The process as set forth in claim 1 wherein the hydrodeoxygenation catalyst support comprises a material selected from the group consisting of carbon, silica and zirconia.

11. The process as set forth in claim 6 wherein the halogen source comprises ionic, atomic, and/or molecular forms of bromine or iodine.

12. The process as set forth in claim 4 wherein the halogen source comprises hydrogen bromide.

13. The process as set forth in claim 1 wherein the molar ratio of the halogen source to C5-backbone substrate is equal to or less than about 1.

14. The process as set forth in claim 5 wherein the reaction is maintained at a temperature of at least about 80° C.

15. The process as set forth in claim 4 wherein the temperature of the reaction is from about 100° C. to about 200° C.

16. The process as set forth in claim 15 wherein the reaction is conducted under a partial pressure of hydrogen ranging from about 25 psia (172 kPa) to about 2500 psia (17237 kPa).

17. The process as set forth in claim 1 wherein at least a portion of the C5-backbone substrate is derived from a pentose.

18. A process for preparing a glutaric acid product, the process comprising:
a) converting at least a portion of a pentose source to a C5-backbone substrate comprising pentaric acid or derivative thereof, and
b) converting, in the presence of a heterogeneous hydrodeoxygenation catalyst comprising at least one d-block metal selected from the group consisting of Co, Ni, Ru, Rh, Pd, Os, Ir, Pt, and combinations thereof at a surface of a support, at least a portion of the pentaric acid or derivative thereof to a glutaric acid product of formula II

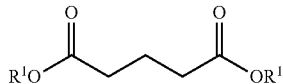

wherein $R^1$ is independently a salt-forming ion, hydrogen, hydrocarbyl, substituted hydrocarbyl, or lactone thereof.

19. The process as set forth in claim 18 wherein the glutaric acid product comprises glutaric acid.

20. The process as set forth in claim 18 wherein the process further comprises converting a source of carbohydrates to the pentose source.

21. A process for preparing a glutaric acid product, the process comprising:
   a) reacting a pentose with oxygen, in the presence of a solvent, and an oxidation catalyst and in the absence of added base, to convert at least a portion of the pentose to at least one pentaric acid and/or derivative thereof, and
   b) reacting, in the presence of a heterogeneous hydrodeoxygenation catalyst comprising at least one d-block metal selected from the group consisting of Co, Ni, Ru, Rh, Pd, Os, Ir, Pt, and combinations thereof at a surface of a support and a halogen source, at least a portion of the at least one pentaric acid and/or derivative thereof and hydrogen, to convert at least a portion of the at least one pentaric acid and/or derivative thereof to a glutaric acid product of formula II

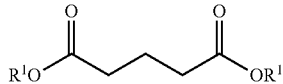

wherein $R^1$ is independently a salt-forming ion, hydrogen, hydrocarbyl, substituted hydrocarbyl, or lactone thereof.

22. The process as set forth in claim 21 wherein a solvent is added to step b) to solubilize the at least one pentaric acid and/or derivative thereof.

23. A process for producing a glutaric acid product from a pentose, the process comprising:
   converting by heterogeneous chemocatalysis at least a portion of the pentose to the glutaric acid product in the presence of a heterogeneous hydrodeoxygenation catalyst comprising at least one d-block metal selected from the group consisting of Co, Ni, Ru, Rh, Pd, Os, Ir, Pt, and combinations thereof at a surface of a support, wherein the glutaric acid product is of formula II

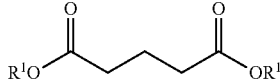

wherein $R^1$ is independently a salt-forming ion, hydrogen, hydrocarbyl, substituted hydrocarbyl, or lactone thereof.

24. The process as set forth in claim 23 wherein the process comprises:
   a) converting by chemocatalysis at least a portion of the pentose to pentaric acid or derivative thereof, and
   b) converting by heterogeneous chemocatalysis at least a portion of the pentaric acid or derivative thereof to the glutaric acid product.

25. The process as set forth in claim 24 wherein the glutaric acid product comprises glutaric acid.

26. The process of claim 24 wherein the pentose comprises xylose and the pentaric acid or derivative thereof comprises xylaric acid or derivative thereof.

27. The process of claim 24 wherein the pentaric acid is xylaric acid.

28. A process of claim 21 wherein the oxygen is supplied to the reaction as air, oxygen-enriched air, oxygen alone, or oxygen with one or more other constituents substantially inert to the reaction.

29. The process as set forth in claim 21 wherein at least a portion of the at least one pentaric acid and/or derivative is solubilized with a weak carboxylic acid.

30. The process as set forth in claim 21 wherein the hydrodeoxygenation catalyst comprises a d-block metal selected from the group consisting of Ru, Rh, Pd, Pt, and combinations thereof.

31. The process as set forth in claim 21 wherein the halogen source comprises ionic, atomic, and/or molecular forms of bromine or iodine.

32. The process as set forth in claim 29 wherein the halogen source comprises hydrogen bromide.

33. The process as set forth in claim 7 wherein the d-block metal is selected from the group consisting of Ru, Rh, Pd, Pt, and combinations thereof.

34. The process as set forth in claim 10 wherein the d-block metal is selected from the group consisting of Ru, Rh, Pd, Pt, and combinations thereof.

35. The process as set forth in claim 1 wherein the glutaric acid product comprises glutaric acid.

36. The process as set forth in claim 21 wherein the glutaric acid product comprises glutaric acid.

* * * * *

UNITED STATES PATENT AND TRADEMARK OFFICE
CERTIFICATE OF CORRECTION

PATENT NO. : 8,785,683 B2
APPLICATION NO. : 12/814216
DATED : July 22, 2014
INVENTOR(S) : Boussie et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 517 days.

Signed and Sealed this
Ninth Day of February, 2016

Michelle K. Lee
*Director of the United States Patent and Trademark Office*